United States Patent [19]

Lafaut et al.

[11] Patent Number: 6,123,679

[45] Date of Patent: *Sep. 26, 2000

[54] METHOD FOR EXTRACORPOREAL SHOCK WAVE LITHOTRIPSY BY APPLYING AN ACOUSTIC SHOCK WAVE FOLLOWED BY A LIMITED OSCILLATING ACOUSTIC PRESSURE WAVE TRAIN

[76] Inventors: Jean-Pierre Lafaut, Doornikserijksweg 54, B8510 Bellegem; Luc Baert, Berkenhoflaan 31, B3001 Heverlee; Geert Pittomvils, Dr. Folletlaan 220, B1780 Wemmel; Hendrik Vandeursen, Zandstraat 52, B3140 Keerbergen; Martine Wevers, Martelarenstraat 15, B3370 Boutersem, all of Belgium

[ * ] Notice: This patent issued on a continued prosecution application filed under 37 CFR 1.53(d), and is subject to the twenty year patent term provisions of 35 U.S.C. 154(a)(2).

[21] Appl. No.: 08/705,121

[22] Filed: Aug. 29, 1996

[51] Int. Cl.$^7$ ........................................... A61B 17/22
[52] U.S. Cl. ................................. 601/4; 600/439
[58] Field of Search .................. 601/2, 3, 4; 128/660.03; 604/22, 49; 600/439

[56] References Cited

U.S. PATENT DOCUMENTS

| | | |
|---|---|---|
| 4,907,573 | 3/1990 | Nagasaki . |
| 4,972,826 | 11/1990 | Koehler et al. . |
| 5,105,801 | 4/1992 | Cathignol et al. . |
| 5,158,070 | 10/1992 | Dory . |
| 5,219,401 | 6/1993 | Cathignol et al. . |
| 5,380,411 | 1/1995 | Schlief . |
| 5,582,578 | 12/1996 | Zhong et al. . |
| 5,601,526 | 2/1997 | Chapelon et al. . |
| 5,618,275 | 4/1997 | Bock . |

OTHER PUBLICATIONS

Field, J.E. The Physics of Liquid Impact, Shock Wave Interactions with Cavities, and the Implications to Shock Wave Lithotripsy, Phys. Med. Biol. 36, 1475–1484, 1991.

Noltingk et al., "Cavitation Produced by Ultrasonics," Proc. Phys. Soc. London 63, 674–685, 1950.

Lauterborn "Numerical Investigation of Nonlinear Oscillations of Gas Bubbles in Liquids," U.Acoust. Soc. Am. 59, 283–293, 1976.

Fujiwara et al. Nonlinear Oscillations of Bubbles in Compressible Hydraulic Oils, J. Acoust. Soc. Am. 68, 1502–1508, 1980.

Miksis et al., "Nonlinear Radial Oscillations of a Gas Bubble Including Thermal Effects," J. Acoust. Soc. Am 76, 897–905, 1984.

Prosperetti et al., Nonlinear Bubble Dynamics, J. Acoust. Soc. Am. 83, 502–514, 1988.

Sato et al., Numerical Analysis of a Gas Bubble Near a Rigid Boundary in an Oscillatory Pressure Field, J. Accoust. Soc. Am 95, 2416–2424, 1994.

Flynn, Physical Acoustics, Principles and Methods, vol. 1, part B: "Physics of Acoustic Cavitation in Linquids," 78–172, 1964 (ed. W.P. Mason) Academic Press, New York and London.

Vogel et al, "Optical and Acoustic Investigations of the Dynamics of Laser–produced Cavitation Bubbles Near a Solid Boundary," J. Fluid Mech. 206, 299–338, 1989.

Rayleigh, "On the Pressure Developed in a Liquid During the Collapse of a Spherical Cavity," Phil. Mag. 34, 94–98, 1917.

(List continued on next page.)

*Primary Examiner*—Marvin M. Lateel
*Assistant Examiner*—Shawna J. Shaw
*Attorney, Agent, or Firm*—Hill & Simpson

[57] ABSTRACT

A method for extracorporeal shock wave lithotripsy comprises the steps of applying to a concretion to be disintegrated an acoustic shock wave and applying to the concretion to be disintegrated in sequence to said acoustic shock wave an oscillating acoustic pressure wave train having a pressure amplitude, said oscillating acoustic wave train having at least one amplitude maximum and at least one amplitude minimum.

24 Claims, 4 Drawing Sheets

OTHER PUBLICATIONS

Zhong et al. "Characterization of Fracture Toughness of Renal Calculi Using Microindentation Technique," J. Mat. Sci, Lett. 12, 1460–1462, 1993.

Dretler "Stone Fragility—A New therapeutic Distinction," J. Urol. 139, 1124–1127, 1988.

Pittomvils et al., "The Influence of the internal Stone Structure upon the Fracture of Urinary Calculi," Ultrasound med. Biol. 20, 803–810, 1994.

Vandeursen et al., "High Pressure Versus Low Pressure Electromagnetic Extracorporeal Shock Wave Lithotripsy," J. Urol. 149, 988–991, 1993.

METHOD FOR EXTRACORPOREAL SHOCK WAVE LITHOTRIPSY BY APPLYING AN ACOUSTIC SHOCK WAVE FOLLOWED BY A LIMITED OSCILLATING ACOUSTIC PRESSURE WAVE TRAIN

FIELD OF THE INVENTION

The invention relates to a method for extracorporeal shock wave lithotripsy, i.e. a method for disintegrating concretions, e.g. kidney stones, in the living body of a living being, especially a human patient, by the application of acoustic shock waves. A shock waves is a positive acoustic pressure pulses having a very steep leading edge (rise time e.g. 0,1 to 5 microseconds ($\mu$s)).

DESCRIPTION OF THE PRIOR ART

It is suggested, that cavitation plays an important role in the disintegration of concrements during Extracorporeal Shock Wave Lithotripsy (ESWL). The mechanisms responsible for cavitation formation during ESWL are still poorly understood, nevertheless.

Cavitation bubble generation has often been related to the liquid failure induced by the rarefaction zone of the extracorporeally generated shock wave (see references (1) and (2) as listed at the end of this specification). The generation of a large cavitation bubble (several millimeters in diameter) at the anterior interface plane of the target, i.e. the concrement to be disintegrated, has been related to the impedance mismatch at that plane, however. It has been suggested that a large hemispherical cavitation bubble, attached to the liquid/target interface, is generated in the wake of the shock wave reflected from the target.

A fiber optic sensing technique has shown the importance of ESWL-induced cavitation in the disintegration of kidney stones. The induced stress generated in the fiber at the moment of bubble implosion exceeds the stress generated during shock wave incidence. The transmission of acoustic energy to a concrement, for instance a kidney stone, however, is less than the energy transfer seen during shock wave incidence.

(Ultra)Sonic stimulation, i.e. acoustic stimulation, of a cavitation bubble in a liquid has been known for more than forty years (see reference (3) as listed at the end of this specification). Computer simulations suggest that the radius of the cavitation bubble can be enlarged by 100% or more by the use of acoustic stimulation (see references (4) to (9) as listed at the end of this specification).

OBJECTS OF THE INVENTION

It is an object of the present invention to provide a lithotripsy method which allows for using cavitation energy more effectively for the disintegration of concretions.

SUMMARY OF THE INVENTION

The above object is achieved by applying an acoustic shock wave to a concretion to be disintegrated; and applying to the concretion to be disintegrated in sequence to the acoustic shock wave an oscillating acoustic pressure wave train having a pressure amplitude, the oscillating acoustic pressure wave train having at least one amplitude maximum and at least one amplitude minimum.

It has been found, that the application of such an oscillating acoustic pressure wave train results in increasing the cavitation bubble present after the application of the shock wave. This increased cavitation bubble size in turn results in a greater contribution of the cavitation bubble implosion on the disintegration effectiveness, as a doubling in bubble size results in an energy gain of the acoustic transient at the implosion of the cavitation bubble of about 700%. Such an enormous energy gain for the acoustic transient towards the kidney stones at the moment of bubble implosion, is possible, since the energy stored in the cavitation bubble is proportional to the third power of its radius (see references (10) and (11) as listed at the end of this specification). It is to be understood, that an acoustic shock wave with a peak pressure sufficient to produce at least one cavitation bubble in the region of the concretion to be disintegrated has to be applied. As it will be sufficient in only a very number of cases to apply a single shock wave followed by an oscillating acoustic pressure wave train to disintegrate a concrement, a preferably periodic sequence of shock waves, each followed by an oscillating acoustic pressure wave train, will normally be applied.

Depending on the cavitation bubble size finally reached, the above-mentioned possible energy gain can have the result that more energy is transferred to the concrement at the moment of bubble implosion than during shock wave incidence. This is possible for all acoustic impedance values for concrements, i.e. kidney stones. Even kidney stones of calcium oxalate monohydrate with a high resistance to fracture stones (see references (14) to (16) as listed at the end of this specification) can thus easily be disintegrated by the inventive method without the need for anaesthetic requirements. This is an important advantage over the prior art, as the major advantage of extracorporeal lithotripsy on endourological techniques is lost, when anaesthesia has to be performed. Nevertheless, for lithotripsy certain limitations must be taken into account, namely the cavitation threshold, the absorption in the surrounding tissue and the disturbing noise generation during application.

The term of wave train as used in this specification and the appended claims is to describe a wave train having a limited duration. Therefore, one example for an oscillating acoustic pressure wave train is an (ultra)sound burst the duration of which comprises a plurality of half periods of a sinusoidal wave form.

The further object of the invention of improving disintegration effectiveness without the danger of tissue damages is achieved by focussing the acoustic shock wave and/or the oscillating acoustic pressure wave train.

Another object of the invention is to allow for a technically simple generation of the oscillating acoustic pressure wave train. This object is reached by applying an oscillating acoustic pressure wave train having a sinusoidal wave shape. As the cavitation bubble size finally reached, at least to some degree, increases with duration of the oscillating acoustic pressure wave train, the oscillating acoustic pressure wave train has a duration of more than one period of the sinusoidal wave shape.

The cavitation bubble size, and thus the disintegration effectiveness finally reached increases the lower the frequency of the acoustic pressure wave train is. As far as the goal of disintegration effectiveness is concerned the frequency of the oscillating acoustic pressure wave train should be as low as possible, preferably below 16 kilohertz (kHz). As too low a frequency of the oscillating acoustic pressure wave train might cause discomfort due to vibratory sensations and noise to the patient as well as to the personnel attending lithotripsy due to noise, the oscillating acoustic pressure wave train may have a frequency above 16 kHz.

The object of the invention of at least doubling the diameter of the cavitation bubble present after the application of an acoustic shock wave is achieved by applying an oscillating acoustic pressure wave train whose pressure amplitude in Pa at least equals 350 times the frequency of said acoustic oscillating wave train in hertz (Hz).

Normally, an acoustic shock wave is followed by an decay process comprising a sequence of undershoots and overshoots. In terms of disintegration effectiveness the optimal moment for applying the oscillating acoustic pressure wave train is then immediately following one of the undershoots, preferably immediately following the first undershoot, as immediately after the first undershoot cavitation bubble size is maximum.

BRIEF DESCRIPTION OF THE DRAWINGS

For a better understanding of the invention reference should be made to the accompanying drawings in which there are illustrated a preferred embodiment and diagrams explaining this preferred embodiment of the invention.

DETAILED DESCRIPTION

Figure 1:
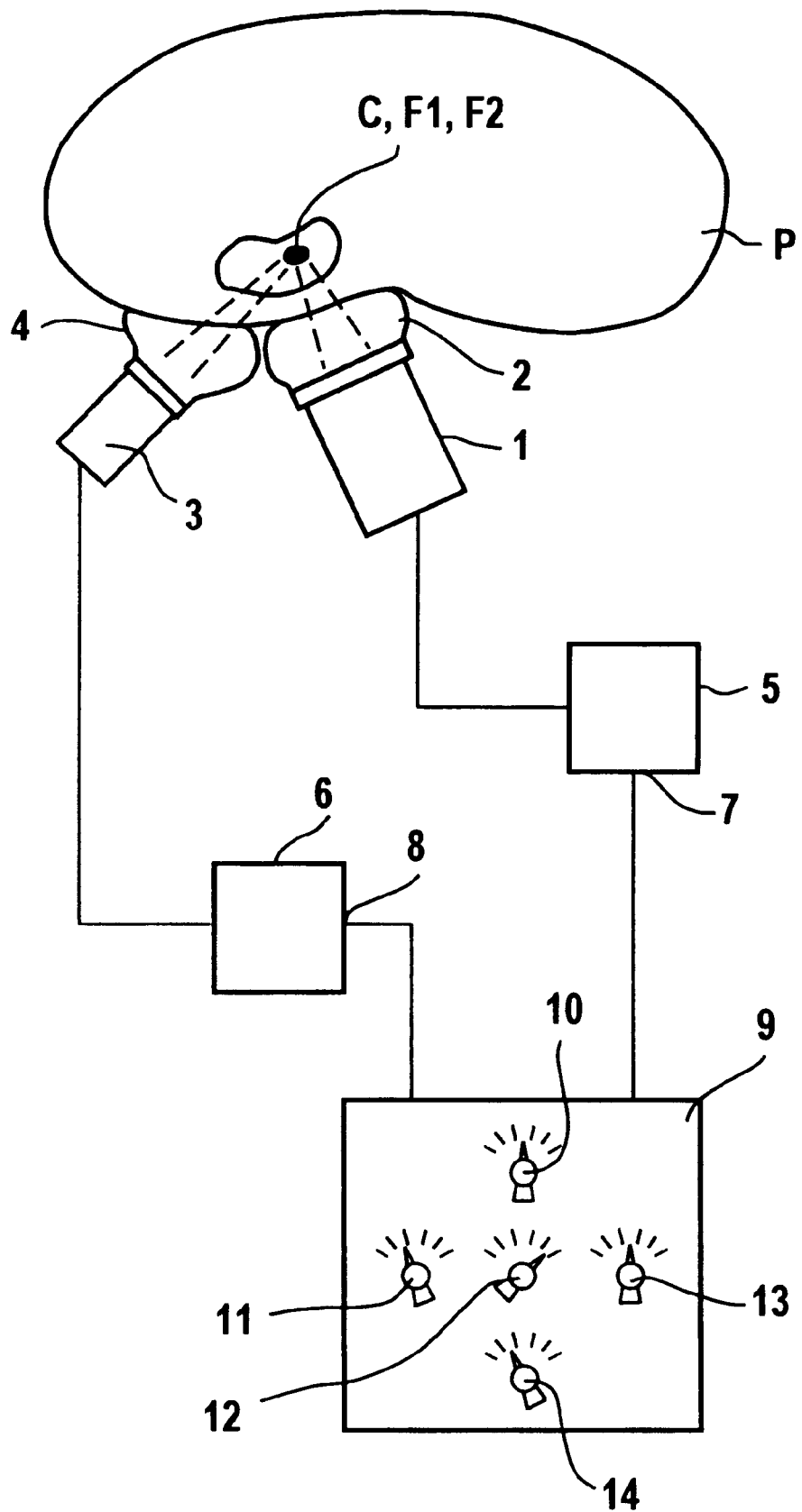
FIG. 1 shows schematically ESWL according to the present invention using acoustic shock waves and an oscillating acoustic pressure wave train being administered to a patient.

FIG. 1 shows an acoustic shock wave generator 1, which is for instance of the type described in detail in U.S. Pat. No. 4,674,505, the disclosure of which is herewith incorporated by reference.

The shock wave generator 1 serves the purpose of applying acoustic shock waves focussed to a focus zone, the center of which is referenced F1, to a concretion, for instance a kidney stone C, in the body of a patient P.

The generator 1 is acoustically coupled to the body of the patient P by means of a flexible application bellows 2, sealing the generator 1, which is filled with a liquid acoustic propagation medium.

The generator 1 and the body of the patient P are positioned relative to one another by means of a conventional X-ray or ultrasound locating system such that the center of the focus zone F1 of the shock waves is located at the concretion C.

Also applied to the body of the patient P is a conventional therapeutic sound source, which is capable of generating oscillating acoustic pressure wave trains of sinusoidal wave shape, having a pulse length or limited duration. These wave trains, which could also be referred to as sound bursts, are also focussed to a focus zone, the center of which is referenced F2. The sound source 3 and the body of the patient P as well are positioned relative to one another by means of the locating system mentioned above or by means of an additional conventional X-ray or ultrasound locating system such that the center of the focus zone F1 of the oscillating acoustic pressure wave trains is located at the concretion C.

Also the sound source 3 is applied to the body of the patient P by means of a flexible application bellows, which is referenced 4. The sound source 3 is for instance of the type described in U.S. Pat. No. 4,658,828, the disclosure of which is herewith incorporated by reference.

The shock wave generator 1 and the sound source 3 can also be mounted in a common housing with a common application bellows, as for instance described in U.S. Pat. No. 4,976,255, the disclosure of which is herewith incorporated by reference.

Electrical drive circuits 5 and 6 are connected to the shock wave generator 1 and the sound source 3, respectively. Both electrical drive circuits 5 and 6 have a trigger input 7 and 8 which is connected by means of a control line to a control unit 9. The shock wave generator 1 is driven by drive circuit 6 to generate a shock wave, when a trigger pulse emitted by control circuit 9 reaches trigger input 7. The sound source 3 is driven by drive circuit 5 to generate an oscillating acoustic pressure wave train, when a trigger pulse emitted by control circuit 9 reaches trigger input 8.

Electrical drive circuit 5 which is allocated to the shock wave generator 1 allows for setting the peak pressure amplitude of the generated shock waves. This is indicated in FIG. 1 by an adjusting knob 10.

Electrical drive circuit 6 which is allocated to the sound source 3 allows for setting amplitude, frequency and pulse length, i.e. duration, of the oscillating acoustic pressure wave trains. This is indicated in FIG. 1 by respective adjusting knobs 11 to 13.

During lithotripsy, the control unit 9 sends a periodic sequence of first trigger pulses to electrical drive circuit 5 via the respective control line. After each first trigger pulse control unit 9 sends a second trigger pulse to electrical drive circuit 6 via the respective control line.

The control unit 9 is provided with a further adjusting knob 14 which serves for adjusting the delay time between the first and second trigger pulses.

Figure 2:
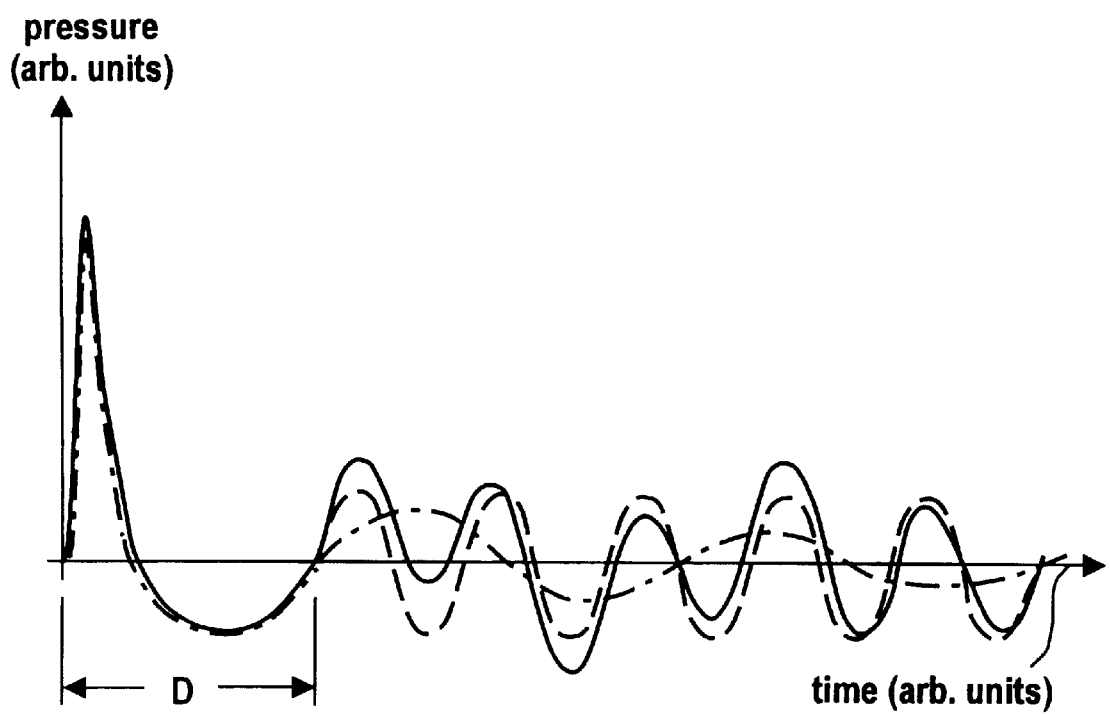
FIGS. 2 and 3 show the wave forms of an ESWL-induced shock wave in a dotted broken line and of the oscillating acoustic pressure wave train in a broken line as well as the wave form resulting from the application of these two wave forms for two different timings of applications in a full line.

If the adjusted delay time is minimum, the phase shift between the first and second trigger pulses is such, that the oscillating acoustic pressure wave train is applied immediately following the first undershoot of the decay process of the shock wave. The resulting wave form at the site of the concrement C as a function of time is represented in FIG. 2, which also shows, that the damped decay process of the shock wave comprises a sequence of undershoots and overshoots.

Figure 3:
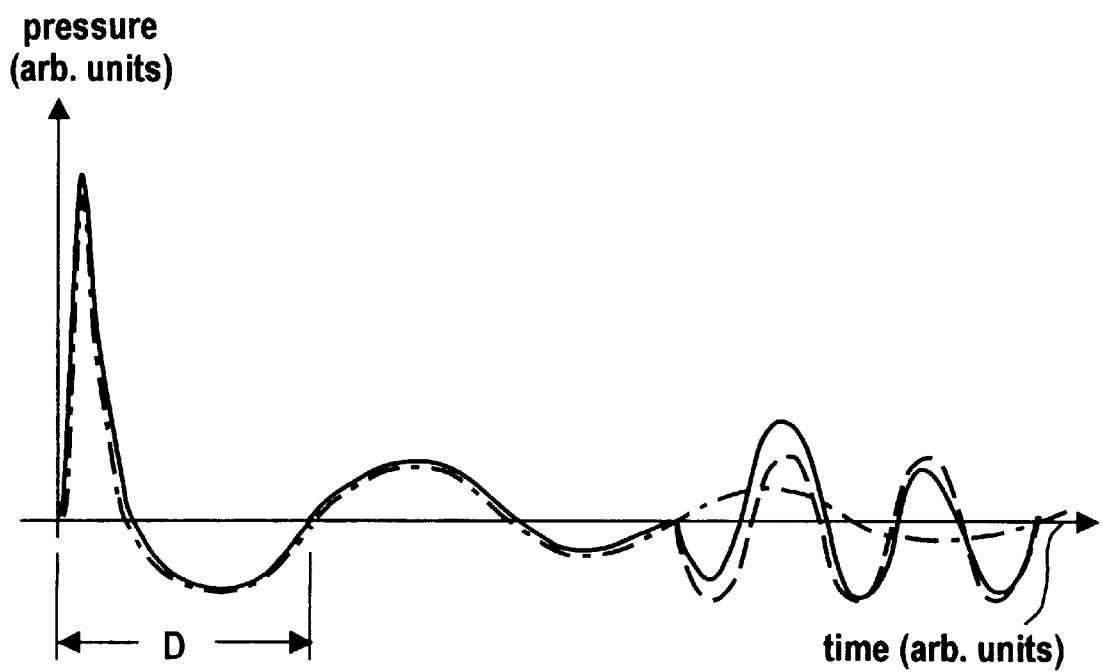

If the adjusted delay time is greater then minimum, the phase shift between the first and second trigger pulses is such that oscillating acoustic pressure wave train is applied immediately following one of the undershoots of the decay process of the shock wave. An exemplary resulting wave form at the site of the concrement C as a function of time is represented in FIG. 3.

If the intensity, i.e. the peak pressure, of the shock waves is adjusted such, that cavitation occurs at the site of the concrement C, the resulting cavitation bubbles are blown up, so to say, by the application of the oscillating acoustic pressure wave train. As the energy induced in the concrement C by the collapse of a cavitation bubble is the higher the greater the diameter of the cavitation is, the collapsing of the blown up cavitation bubbles results in an additional energy transfer to the concrement C, and thus an increased disintegrating efficiency.

For most uses of the invention the peak pressure amplitude of the shock waves can be set in a range from about $10 \times 10^6$ to $100 \times 10^6$ pascal(Pa), i.e. 10 to 100 megapascal (MPa).

For most uses of the invention the pulse length of the oscillating acoustic pressure wave trains can be set in a range from about 100 $\mu$s to some milliseconds (ms) and the amplitude of the oscillating acoustic pressure wave trains can be set in a range from about some $10^5$ to some $10^7$ Pa, i.e. 0,1 to 10 MPa. For most uses of the invention the delay time between the first and second trigger pulses can be set in a range from about 10 $\mu$s to some 100 $\mu$s. The frequency of the oscillating acoustic pressure wave trains can be set in a range from about 1 to 25 kHz.

Amplitude, frequency and duration of the oscillating acoustic pressure wave trains are preferably set such, that the application of the oscillating acoustic pressure wave trains results in doubling the diameter of the cavitation bubbles.

In order to find an explanation for the improved disintegration effectiveness of the lithotripsy method according to the invention, computer simulations of sonic stimulation on ESWL-induced cavitation bubbles were performed.

Figure 4:
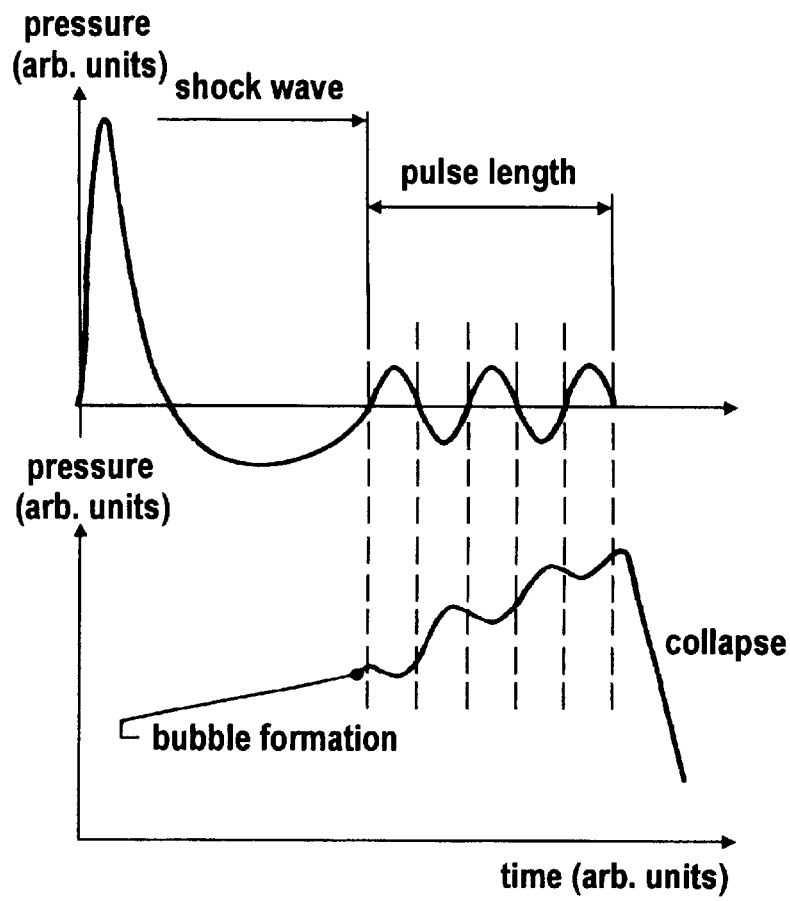
FIG. 4 shows on top an ESWL-induced shock wave followed by a pressure wave train and below the time course of the radius of the induced cavitation bubble following irradiation with an oscillating acoustic pressure wave train.

These computer simulations were based on the addition of an oscillating acoustic pressure wave train of a particular intensity (amplitude), frequency and pulse length to the shock wave, as represented in FIG. 4, with the shock wave having an intensity sufficient to produce a cavitation bubble at the site of the concretion to be disintegrated.

Because of its simplicity, the equation of motion for a cavitation bubble surface in a non-viscous fluid, derived by Rayleigh (see reference (12) as listed at the end of this specification) is widely used. The computer simulations were based on the Rayleigh equation in its best-known form:

$$p_{fl}\{R(t)R''(t)+1.5\ R'^2(t)\}=p_g-2\sigma/R(t)-p_{fl}(\infty) \qquad \text{eqn. (1),}$$

wherein $p_{fl}$ is the density of the fluid;

R(t) is the radius of curvature of the interface as a function of time t;

$\sigma$ is the surface tension of the fluid;

$p_{fl}(\infty)$ is the pressure in the fluid at infinity;

$p_g$ is the pressure of the vapour/gas mixture trapped in the cavitation bubble; and R'(t) and R''(t) are the first and second derivatives of the radius as functions of time t.

The adiabatic behaviour of the vapour/gas mixture trapped in the cavitation bubble is expressed by $$pV^k=A,$$

wherein

A is a constant; and

K is the ratio of the molar specific heats of the gases, i.e. $K=C_p/C_v$.

This means that $$p_g=p_i(R_i/R_f)^{3k},$$

wherein $p_i$ is the initial pressure corresponding to the radius $R_i$;

$R_i$ is the initial bubble radius; and $R_f$ is the final bubble radius.

An additional variable sine wave shaped oscillating acoustic pressure wave train in the surrounding liquid at infinity with a frequency f and amplitude p' (both variable parameters) is added:

$$p_{fl}(\infty)=p_{atm}-p'\sin(2\pi ft),$$

wherein f is the frequency of the sine wave $p_{atm}$ is the atmospheric pressure; and p is the pressure amplitude of the sine wave.

After substituting $p_g$ and $p_{fl}(\infty)$ in eqn. (1)

$$p_{fl}\{R(t)\ R''(t)+1.5\ R'^2(t)\}=p_i(R_i/R(t))^{3k}-2\ \sigma/R(t)-p_{atm}+p'\sin(2\pi ft) \qquad \text{eqn. (2).}$$

is obtained.

This equation, i.e. eqn. (2), is solved for a specific pressure amplitude in a certain frequency interval in order to determine how the initial radius R(0) changes.

The calculations were performed using a general software program, Mathematica (see reference (13) as listed at the end of this specification).

The values for the physical constants used for the calculations were those of a vapour bubble in water at 20° C., i.e. $p_{fl}$=998.2 kg/m$^3$; $p_i$=2340 Pa; k=1.33; $\sigma$=72.8 $10^{-3}$ N/m$^2$ (Newton per square meter); $p_{atm}$=1.013 $10^5$Pa; R(0)=2 $10^{-3}$ m; R'(0)=0.

The initial radius of the cavitation bubble depends on the impedance mismatch at the water/target interface, the absorption characteristics of the ESWL-shock wave and the energetic correlation between the bubble energy and impedance mismatch. An initial bubble radius of 2 mm was used for the computer simulations, as bubbles of this size are supposed to occur in in vivo applications. The computer simulations were based on a pulse length of the oscillating acoustic pressure wave trains of 1000 $\mu$s (1.e. 1 ms).

Figure 6:
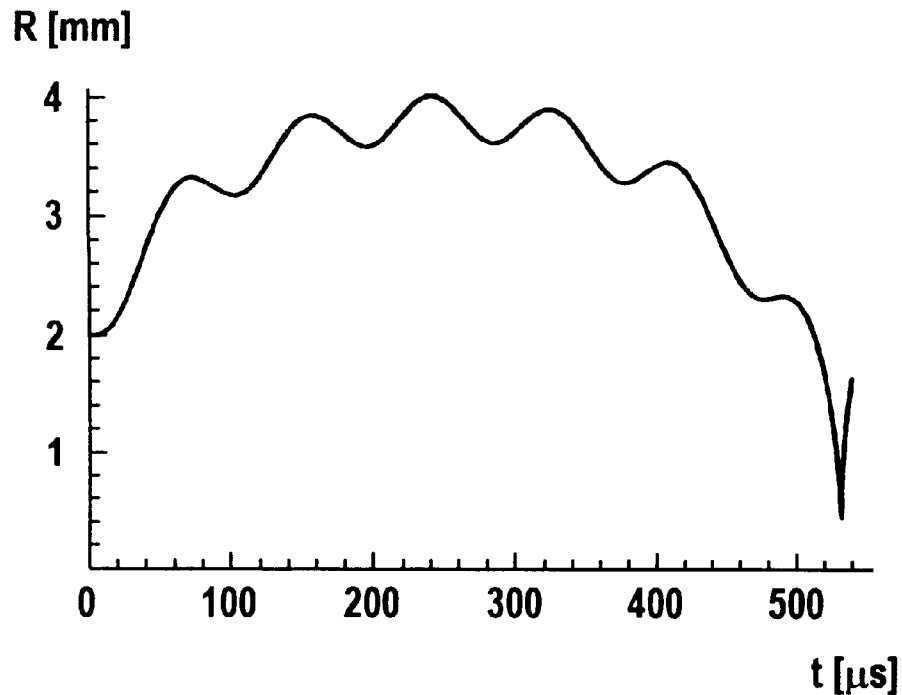
FIG. 6 shows as a function of time the radius of a cavitation bubble produced by application of an ESWL-induced shock wave following irradiation with an oscillating acoustic pressure wave train of fixed amplitude and frequency, 3600 kPa and 11.3 kHz respectively.
Figure 7:
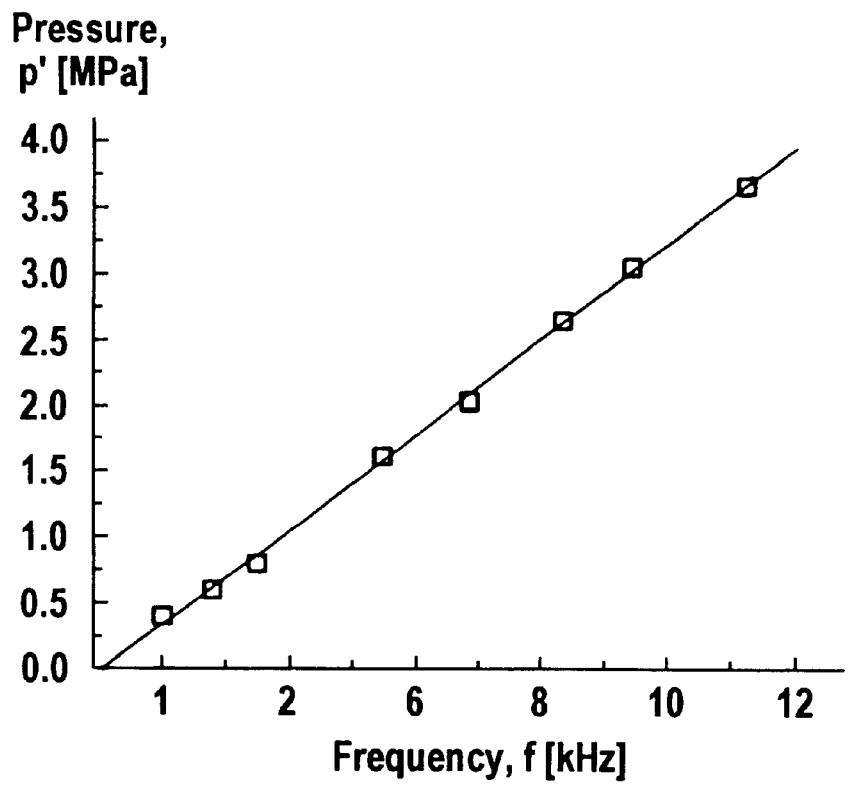
FIG. 7 shows the relationship between the amplitude and frequency of an oscillating acoustic pressure wave train required to double the radius of a cavitation bubble.

The results of the computer simulations will now be discussed with reference to FIGS. 5 to 7.

Figure 5:
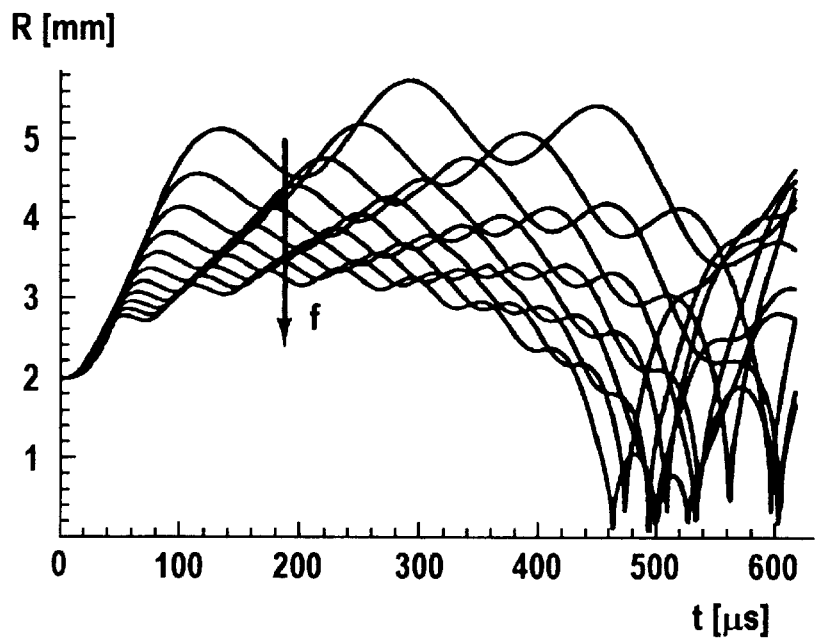
FIG. 5 shows as a function of time the radius of a cavitation bubble produced by application of an ESWL-induced shock wave following irradiation with an oscillating acoustic pressure wave train of fixed amplitude (3600 kPa) and a variable frequency (6 to 16 kHZ, step 1 kHz), with ↓ f indicating an increase in frequency.

FIG. 5. shows bubble radius as a function of time at a fixed pressure amplitude (p'=3600 kPa) and a variable frequency (f varies from 6 to 16 kHz, step 1 kHz) of the added sound wave. The forced oscillation of the cavitation bubble indicates the frequency of the added oscillating acoustic pressure wave train with a low frequency corresponding to a low oscillating frequency (FIG. 5).

At a fixed pressure amplitude, lowering the frequency results in an increase in bubble lifetime and bubble size. The considerable increase in bubble radius (more than 6-fold for a 2 kHz sonic stimulation at 3600 kPa) seen at low frequencies was also seen in a previous theoretical study of a cavitation bubble with a radius of 5 mm (see reference (9) as listed at the end of this specification). The radius of the 2 mm bubble is doubled at a frequency of 11.3 kHz at a pressure amplitude of 3600 kPa. A detailed plot of the oscillating behaviour of the bubble stimulated by this 11.3 kHz pressure wave is shown in FIG. 6.

A similar doubling of radius was investigated for seven different fixed pressure amplitudes, namely 400, 600, 800, 1600, 2000, 2600 and 3000 kPa. The frequencies at which doubling occurred are plotted in FIG. 7; a linear fit (correlation coefficient 0.999) was seen with a slope equal to 351 Pa/Hz, which makes it possible to calculate the values for the parameters (pressure amplitude and frequency) needed to obtain doubling of the initial radius.

While the invention has been described in terms of a preferred embodiment, those skilled in the art will appreciate that various modifications, substitution, omissions and changes may be made without departing from the spirit thereof. Accordingly, it is intended that the scope of the invention be limited solely by the scope of the following claims.

REFERENCES (1) Field, J. E. The physics of liquid impact, shock wave interactions with cavities, and the implications to shock wave lithotripsy. Phys. Med. Biol. 36,1475–1484,1991.
(2) Holmer, N.-G.; Almquist, L.-O. Hertz, T. G.; Holm A.; Lindstedt, E.; Persson, H. W.; Hertz, C. H. On the mechanism of kidney stone disintegration by acoustic shock waves. Ultrasound Med. Biol. 17, 479–489,1991.
(3) Noltingk, B. E.; Neppiroas, E. A. Cavitation produced by ultrasonics. Proc. Phys. Soc. London 63, 674–685,1950.
(4). Lauterborn, W. Numerical investigation of nonlinear oscillations of gas bubbles in liquids. J. Acoust. Soc. Am. 59, 283–293,1976.
(5) Fujiwara, T.; Shima, A. Nonlinear oscillations of bubbles in compressible hydraulic oils. J. Acoust. Soc. Am. 68, 1502–1508, 1980.
(6) Miksis, M. J.; Ting, L. Nonlinear radial oscillations of a gas bubble including thermal effects. J. Acoust. Soc. Am. 76, 897–905, 1984.
(7) Prosperetti A.; Crum, L. A.; Commander K. W. Nonlinear bubble dynamics. J. Acoust. Soc. Am. 83, 502–514, 1988.
(8) Sato, K.; Tomita, Y.; Shima, A. Numerical analysis of a gas bubble near a rigid boundary in an oscillatory pressure field. J. Acoust. Soc. Am. 95, 2416–2424, 1994.
(9) Flynn, H. G. Physical Acoustics, principles and methods, volume 1, part B : Physics of acoustic cavitation in liquids. 78–172, 1964. (ed. W. P. Mason) Academic Press, New York and London.
(10) Vogel, A.; Lauterborn, W. Acoustic transient generation by laser-produced cavitation bubbles near solid boundaries. J. Acoust. Soc. Am. 84, 719–731,1988.
(11) Vogel, A.; Lauterbom, W.; Timm, R. Optical and acoustic investigations of the dynamics of laser-produced cavitation bubbles near a solid boundary. J. Fluid Mech. 206, 299–338, 1989.
(12) Rayleigh L.: On the pressure developed in a liquid during the collapse of a spherical cavity. Phil. Mag. 34, 94–98, 1917.
(13) Stephen W.: Mathematica : A system for doing mathematics by computer. Second edition, Addison-Wesley Plublishing Company, 1991.
(14) Zhong, P.; Chuong, C. J.; Preminger, G. M. Characterization of fracture thoughness of renal calculi using microindentation technique. J. Mat. Sci. Lett. 12, 1460–1462, 1993.
(15) Dretler, S. P. Stone fragility—a new therapeutic distinction. J. Urol. 139, 1124–1127,1988.
(16) Pittomvils, G.; Vandeursen, H.; Wevers, M.; Lafaut, J. P.; De Ridder, D.; De Meester, P.; Boving, R.; Baert, L. The influence of the internal stone structure upon the fracture behaviour of urinary calculi. Ultrasound Med. Biol. 20, 803–810, 1994.
(17) Vandeursen, H.; De Ridder, D.; Pittomvils, G.; Demeulenaere, R.; Herremans, D.; Boving, R.; Baert, L. High pressure versus low pressure electromagnetic extracorporeal shock wave lithotripsy. J. Urol. 149, 988–991, 1993.

What is claimed is:

1. A method for extracorporeal shock wave lithotripsy comprising the steps of:
   applying an acoustic shock wave to a concretion to be disintegrated in a body, said acoustic shock wave having a peak amplitude which produces cavitation in said body in a region of said concretion; and
   following said shock wave, applying to the concretion a limited oscillating acoustic pressure wave train having a pressure amplitude and a frequency below 16 kHz, said limited oscillating acoustic pressure wave train having at least one pressure amplitude maximum and at least one pressure amplitude minimum and altering said cavitation to enhance disintegration of said concretion.

2. A method as claimed in claim 1 comprising the further step of focusing said acoustic shock wave.

3. A method as claimed in claim 1 comprising the further step of focusing said limited oscillating acoustic pressure wave train.

4. A method as claimed in claim 1 wherein said step of applying said limited oscillating acoustic pressure wave train is further defined by applying an oscillating acoustic pressure wave train having sinusoidal wave shape.

5. A method as claimed in claim 4 wherein said limited oscillating acoustic pressure wave train has a duration of more than one period of said sinusoidal wave shape.

6. A method as claimed in claim 1 wherein said acoustic shock wave is followed by a decay process comprising a sequence of undershoots and overshoots, and said step of applying said limited oscillating acoustic pressure wave train is further defined by applying said limited oscillating acoustic pressure wave train immediately following one of said undershoots.

7. A method as claimed in claim 6 wherein said decay process comprises a first undershoot and wherein said limited oscillating acoustic pressure wave train is applied immediately following said first undershoot.

8. A method as claimed in claim 1 wherein said acoustic shock wave is followed by a decay process comprising an undershoot, and said step of applying said limited oscillating acoustic pressure wave train is further defined by applying said limited oscillating acoustic pressure wave train immediately following said undershoot.

9. A method as claimed in claim 1 wherein said cavitation in said body in a region of said concretion comprises at least one bubble having a radius, and wherein the step of altering said cavitation to enhance disintegration of said concretion comprises increasing said radius by applying said limited oscillating acoustic pressure wave train.

10. A method as claimed in claim 9 wherein the step of increasing said radius comprises at least doubling said radius.

11. A method as claimed in claim 1 wherein said cavitation in said body in said region of said concretion comprises at least one bubble, said bubble, upon implosion, producing an acoustic transient having an energy associated therewith, and wherein the step of altering said cavitation to enhance disintegration of said concretion comprises altering said cavitation to increase the energy of said acoustic transient upon implosion of said at least one bubble.

12. A method as claimed in claim 11 wherein the step of increasing the energy comprises increasing the energy by at least 700%.

13. A method for extracorporeal shock wave lithotripsy comprising the steps of:

applying an acoustic shock wave to a concretion to be disintegrated in a body, said acoustic shock wave having a peak amplitude which produces cavitation in said body in a region of said concretion; and following said shock wave, applying to the concretion a limited oscillating acoustic pressure wave train having a frequency in Hz and a pressure amplitude in Pa at least equaling 350 times said frequency in Hz, said limited oscillating acoustic pressure wave train having at least one pressure amplitude maximum and at least one pressure amplitude minimum and altering said cavitation to enhance disintegration of said concretion.

14. A method as claimed in claim 13 comprising the further step of focusing said acoustic shock wave.

15. A method as claimed in claim 13 comprising the further step of focusing said limited oscillating acoustic pressure wave train.

16. A method as claimed in claim 13 wherein said step of applying said limited oscillating acoustic pressure wave train is further defined by applying an oscillating acoustic pressure wave train having sinusoidal wave shape.

17. A method as claimed in claim 16 wherein said limited oscillating acoustic pressure wave train has a duration of more than one period of said sinusoidal wave shape.

18. A method as claimed in claim 13 wherein said acoustic shock wave is followed by a decay process comprising a sequence of undershoots and overshoots, and said step of applying said limited oscillating acoustic pressure wave train is further defined by applying said limited oscillating acoustic pressure wave train immediately following one of said undershoots.

19. A method as claimed in claim 18 wherein said decay process comprises a first undershoot and wherein said limited oscillating acoustic pressure wave train is applied immediately following said first undershoot.

20. A method as claimed in claim 13 wherein said acoustic shock wave is followed by a decay process comprising an undershoot, and said step of applying said limited oscillating acoustic pressure wave train is further defined by applying said limited oscillating acoustic pressure wave train immediately following said undershoot.

21. A method as claimed in claim 13 wherein said cavitation in said body in a region of said concretion comprises at least one bubble having a radius, and wherein the step of altering said cavitation to enhance disintegration of said concretion comprises increasing said radius by applying said limited oscillating acoustic pressure wave train.

22. A method as claimed in claim 21 wherein the step of increasing said radius comprises at least doubling said radius.

23. A method as claimed in claim 13 wherein said cavitation in said body in said region of said concretion comprises at least one bubble, said bubble, upon implosion, producing an acoustic transient having an energy associated therewith, and wherein the step of altering said cavitation to enhance disintegration of said concretion comprises altering said cavitation to increase the energy of said acoustic transient upon implosion of said at least one bubble.

24. A method as claimed in claim 23 wherein the step of increasing the energy comprises increasing the energy by at least 700%.

* * * * *